US008251985B2

(12) United States Patent
Hoey et al.

(10) Patent No.: US 8,251,985 B2
(45) Date of Patent: Aug. 28, 2012

(54) SYSTEMS AND METHODS FOR TREATMENT OF PROSTATIC TISSUE

(75) Inventors: Michael Hoey, Shoreview, MN (US); John H. Shadduck, Tiburon, CA (US)

(73) Assignee: NxThera, Inc., St. Paul, MN (US)

(*) Notice: Subject to any disclaimer, the term of this patent is extended or adjusted under 35 U.S.C. 154(b) by 163 days.

(21) Appl. No.: 12/614,218

(22) Filed: Nov. 6, 2009

(65) Prior Publication Data
US 2010/0145325 A1 Jun. 10, 2010

Related U.S. Application Data

(60) Provisional application No. 61/112,097, filed on Nov. 6, 2008.

(51) Int. Cl.
*A61B 18/14* (2006.01)

(52) U.S. Cl. .......................... 606/27; 606/41

(58) Field of Classification Search ............ 606/27, 606/28, 41, 45–50; 607/101, 102
See application file for complete search history.

(56) References Cited

U.S. PATENT DOCUMENTS

| | | | |
|---|---|---|---|
| 4,672,963 A | 6/1987 | Barken | |
| 4,950,267 A | 8/1990 | Ishihara et al. | |
| 5,312,399 A | 5/1994 | Hakky et al. | |
| 5,330,518 A | 7/1994 | Neilson et al. | |
| 5,366,490 A | 11/1994 | Edwards et al. | |
| 5,370,609 A | 12/1994 | Drasler et al. | |
| 5,370,675 A * | 12/1994 | Edwards et al. | 607/101 |
| 5,385,544 A | 1/1995 | Edwards et al. | |
| 5,409,453 A | 4/1995 | Lundquist et al. | |
| 5,421,819 A | 6/1995 | Edwards et al. | |
| 5,435,805 A | 7/1995 | Edwards et al. | |
| 5,470,308 A | 11/1995 | Edwards et al. | |
| 5,470,309 A | 11/1995 | Edwards et al. | |
| 5,484,400 A | 1/1996 | Edwards et al. | |
| 5,531,676 A | 7/1996 | Edwards et al. | |
| 5,542,915 A | 8/1996 | Edwards et al. | |
| 5,542,916 A | 8/1996 | Hirsch et al. | |
| 5,545,171 A | 8/1996 | Sharkey et al. | |
| 5,549,644 A | 8/1996 | Lundquist et al. | |
| 5,554,110 A | 9/1996 | Edwards et al. | |
| 5,556,377 A | 9/1996 | Rosen et al. | |
| 5,558,673 A | 9/1996 | Edwards et al. | |
| 5,588,960 A | 12/1996 | Edwards et al. | |

(Continued)

FOREIGN PATENT DOCUMENTS

WO   WO 92/10142 A1   6/1992

(Continued)

OTHER PUBLICATIONS

Shadduck et al.; U.S. Appl. No. 12/614,238 entitled "Systems and Methods for Treatment of Prostatic Tissue," filed Nov. 6, 2009.

(Continued)

*Primary Examiner* — Michael Peffley
(74) *Attorney, Agent, or Firm* — Shay Glenn LLP

(57) ABSTRACT

A prostate therapy system is provided that may include any of a number of features. One feature of the prostate therapy system is that it can access a prostate lobe transurethrally. Another feature of the prostate therapy system is that it can deliver condensable vapor into the prostate to ablate the prostate tissue. Methods associated with use of the prostate therapy system are also covered.

12 Claims, 9 Drawing Sheets

U.S. PATENT DOCUMENTS

| | | | |
|---|---|---|---|
| 5,591,125 A | 1/1997 | Edwards et al. | |
| 5,599,294 A | 2/1997 | Edwards et al. | |
| 5,601,591 A | 2/1997 | Edwards et al. | |
| 5,630,794 A | 5/1997 | Lax et al. | |
| 5,667,488 A | 9/1997 | Lundquist et al. | |
| 5,672,153 A | 9/1997 | Lax et al. | |
| 5,720,718 A | 2/1998 | Rosen et al. | |
| 5,720,719 A | 2/1998 | Edwards et al. | |
| 5,797,903 A | 8/1998 | Swanson et al. | |
| 5,830,179 A | 11/1998 | Mikus et al. | |
| 5,849,011 A | 12/1998 | Jones et al. | |
| 5,871,481 A | 2/1999 | Kannenberg et al. | |
| 5,873,877 A | 2/1999 | McGaffigan et al. | |
| 5,944,715 A * | 8/1999 | Goble et al. | 606/41 |
| 5,957,922 A | 9/1999 | Imran | |
| 5,964,752 A | 10/1999 | Stone | |
| 5,964,756 A | 10/1999 | McGaffigan et al. | |
| 5,976,123 A | 11/1999 | Baumgardner et al. | |
| 6,017,361 A * | 1/2000 | Mikus et al. | 607/105 |
| 6,036,713 A | 3/2000 | Kieturakis | |
| 6,077,257 A | 6/2000 | Edwards et al. | |
| 6,113,593 A | 9/2000 | Tu et al. | |
| 6,206,847 B1 | 3/2001 | Edwards et al. | |
| 6,238,391 B1 | 5/2001 | Olsen et al. | |
| 6,241,702 B1 | 6/2001 | Lundquist et al. | |
| 6,258,087 B1 * | 7/2001 | Edwards et al. | 606/41 |
| 6,423,027 B1 | 7/2002 | Gonon | |
| 6,440,127 B2 * | 8/2002 | McGovern et al. | 606/41 |
| 6,551,300 B1 | 4/2003 | McGaffigan | |
| 6,607,529 B1 | 8/2003 | Jones et al. | |
| 6,669,694 B2 | 12/2003 | Shadduck | |
| 6,716,252 B2 | 4/2004 | Lazarovitz et al. | |
| 6,719,738 B2 | 4/2004 | Mehier | |
| 6,726,696 B1 | 4/2004 | Houser et al. | |
| 6,730,079 B2 | 5/2004 | Lovewell | |
| 6,760,616 B2 | 7/2004 | Hoey et al. | |
| 6,780,178 B2 | 8/2004 | Palanker et al. | |
| 6,827,718 B2 | 12/2004 | Hutchins et al. | |
| 6,905,475 B2 | 6/2005 | Hauschild et al. | |
| 6,969,376 B2 | 11/2005 | Takagi et al. | |
| 7,014,652 B2 | 3/2006 | Cioanta et al. | |
| 7,089,064 B2 | 8/2006 | Manker et al. | |
| 7,130,697 B2 * | 10/2006 | Chornenky et al. | 607/101 |
| 7,261,709 B2 | 8/2007 | Swoyer et al. | |
| 7,261,710 B2 | 8/2007 | Elmouelhi et al. | |
| 7,335,197 B2 | 2/2008 | Sage et al. | |
| 7,429,262 B2 | 9/2008 | Woloszko et al. | |
| 7,470,228 B2 | 12/2008 | Connors et al. | |
| 2002/0177846 A1 | 11/2002 | Mulier et al. | |
| 2003/0069575 A1 | 4/2003 | Chin et al. | |
| 2004/0068306 A1 * | 4/2004 | Shadduck | 607/96 |
| 2004/0230316 A1 | 11/2004 | Cioanta et al. | |
| 2006/0135955 A1 | 6/2006 | Shadduck | |
| 2006/0178670 A1 | 8/2006 | Woloszko et al. | |
| 2006/0224154 A1 | 10/2006 | Shadduck et al. | |
| 2006/0276871 A1 | 12/2006 | Lamson et al. | |
| 2007/0032785 A1 | 2/2007 | Diederich et al. | |
| 2007/0142846 A1 | 6/2007 | Catanese, III et al. | |
| 2008/0021484 A1 | 1/2008 | Catanese, III et al. | |
| 2008/0021485 A1 | 1/2008 | Catanese, III et al. | |
| 2008/0033232 A1 | 2/2008 | Catanese, III et al. | |
| 2008/0033458 A1 | 2/2008 | McLean et al. | |
| 2008/0033488 A1 | 2/2008 | Catanese, III et al. | |
| 2008/0039833 A1 | 2/2008 | Catanese, III et al. | |
| 2008/0039872 A1 | 2/2008 | Catanese, III et al. | |
| 2008/0039874 A1 | 2/2008 | Catanese, III et al. | |
| 2008/0039875 A1 | 2/2008 | Catanese, III et al. | |
| 2008/0039876 A1 | 2/2008 | Catanese, III et al. | |
| 2008/0039893 A1 | 2/2008 | McLean et al. | |
| 2008/0039894 A1 | 2/2008 | Catanese, III et al. | |
| 2008/0046045 A1 | 2/2008 | Yon et al. | |
| 2008/0132826 A1 | 6/2008 | Shadduck et al. | |
| 2008/0208187 A1 | 8/2008 | Bhushan et al. | |
| 2008/0249399 A1 | 10/2008 | Appling et al. | |
| 2008/0275440 A1 | 11/2008 | Kratoska et al. | |
| 2009/0018553 A1 | 1/2009 | McLean et al. | |
| 2009/0054871 A1 | 2/2009 | Sharkey et al. | |
| 2009/0149846 A1 | 6/2009 | Hoey et al. | |
| 2009/0216220 A1 | 8/2009 | Hoey et al. | |
| 2009/0227998 A1 | 9/2009 | Aljuri et al. | |
| 2009/0277457 A1 | 11/2009 | Hoey et al. | |
| 2010/0016757 A1 | 1/2010 | Greenburg et al. | |
| 2010/0049031 A1 | 2/2010 | Fruland et al. | |
| 2010/0286679 A1 | 11/2010 | Hoey et al. | |
| 2010/0292767 A1 | 11/2010 | Hoey et al. | |
| 2010/0298948 A1 | 11/2010 | Hoey et al. | |

FOREIGN PATENT DOCUMENTS

| | | |
|---|---|---|
| WO | WO 01/24715 A1 | 4/2001 |
| WO | WO 2006/004482 A1 | 1/2006 |

OTHER PUBLICATIONS

Hoey et al.; U.S. Appl. No. 12/614,226 entitled "Systems and Methods for Treatment of BPH," filed Nov. 6, 2009.

Shadduck et al.; U.S. Appl. No. 12/687,722 entitled "Systems and Methods for Treatment of Prostatic Tissue," filed Jan. 14, 2010.

Hoey et al.; U.S. Appl. No. 12/687,734 entitled "Medical Systems and Methods," filed Jan. 14, 2010.

Hoey et al.; U.S. Appl. No. 13/072,573 entitled "Systems and Methods for Prostate Treatment," filed Mar. 25, 2011.

Hoey et al.; U.S. Appl. No. 13/352,198 entitled "Systems and methods for prostate treatment," filed Jan. 17, 2012.

Hai; Photoselective Vaporization Prostatectomy: A Palliative Treatment Option for Men with Urinary Obstruction Secondary to Prostate Cancer; PCRI Prost.Cancer Rsrch.Inst. Reprint.from PCRI Insights Nov. 2005, vol. 8(4); Dwnld from http://www.prostate-cancer.org/pcricms/node/233 on May 10, 2012; 4 pages.

* cited by examiner

SYSTEMS AND METHODS FOR TREATMENT OF PROSTATIC TISSUE

CROSS REFERENCE TO RELATED APPLICATIONS

This application claims the benefit under 35 U.S.C. 119 of U.S. Provisional Patent Application No. 61/112,097, filed Nov. 6, 2008, titled "Systems and Methods for Treatment of Prostatic Tissue." This application is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates to an apparatus and a related method for the minimally invasive treatment of prostate tissue.

BACKGROUND OF THE INVENTION

Several systems and methods have been developed or proposed for the treatment of prostate tissue to alleviate BPH symptoms or to treat prostate tissue. For example, tissue ablation methods have been based on RF ablation, microwave ablation, high intensity focused ultrasound (HIFU), cryoablation, radiation, surgery, and brachytherapy. Surgical methods with and without robotic assistance have been developed for removal of diseased prostate tissue.

The apparatus, techniques and methods disclosed herein are adapted to for the treatment of prostate tissue in general and more particularly are focused on treatment of BPH (benign prostatic hyperplasia) and prostate cancer. BPH is a common problem experienced by men over about 50 years old that relates to urinary tract obstruction. Prostatic hyperplasia or enlargement of the prostate gland leads to compression and obstruction of the urethra which results in symptoms such as the need for frequent urination, a decrease in urinary flow, nocturia and discomfort.

Ablation of prostatic tissue with electromagnetic energy is well known and has the advantage of allowing a less invasive approach. For example, high-frequency current in an electrosurgical ablation or prostatic tissue causes cell disruption and cell death. Tissue resorption by the body's wound healing response then can result in a volumetric reduction of tissue that may be causing urinary tract obstruction. One disadvantage of high-frequency current or laser ablation is potential tissue carbonization that results in an increased inflammatory response and far longer healing time following the ablation.

SUMMARY OF THE INVENTION

A method of treating a disorder of a prostate comprises introducing an ablation probe into a lobe of the prostate substantially parallel to a prostatic urethra, and ablating prostate tissue within the lobe without ablating tissue of the prostatic urethra.

Another method of treating a disorder of a prostate adjacent a prostatic urethra comprises delivering condensable vapor into the prostate, and ablating prostate tissue without ablating the prostatic urethra.

Yet another method of treating a disorder of a prostate comprises introducing an ablation probe transurethrally through a urethral wall into an apex of a lobe of the prostate, and ablating prostate tissue in the prostate lobe.

In some embodiments, the introducing step can comprise advancing the ablation probe through a urethral wall into an apex of the prostate lobe. In some embodiments, the introducing step comprises advancing the ablation probe at least 15 mm into the prostate lobe. The introducing step can further comprise advancing an introducer into a urethra and advancing the ablation probe through the introducer. In one embodiment, a port of the introducer can be placed against a urethral wall prior to advancing the ablation probe through the introducer. In another embodiment, at least part of the introducer and at least part of the ablation probe have complementary shapes preventing rotation of the ablation probe with respect to the introducer.

In some embodiments, the ablating step can comprise delivering condensable vapor through the ablation probe into the prostate lobe. The condensable vapor can deliver between 100 and 10,000 Joules to the prostate lobe, or between 20 W and 1000 W to the prostate lobe, or between 100 cal/gm and 600 cal/gm to the prostate lobe.

In some embodiments, the delivering step can comprise delivering condensable vapor into the prostate lobe through a plurality of vapor ports in the ablation probe. The vapor ports can be oriented toward the urethra.

Another embodiment provides a prostate therapy system comprising an ablation probe adapted to be inserted transurethrally into a prostate lobe of an adult male human subject parallel to a prostatic urethra region of the subject, and an energy source operatively connected to the ablation probe to deliver energy to ablate prostate tissue without ablating tissue of the prostatic urethra. The energy source can comprise a condensable vapor source.

The ablation probe can be further adapted and configured to be advanced through a urethral wall and into an apex of the prostate lobe. In one embodiment, the ablation probe is adapted to be inserted at least 15 mm into the prostate lobe. The system can further comprise an introducer adapted to be inserted into an adult human male urethra, the introducer comprising a distal port, the ablation probe being adapted to be advanced into a prostate lobe through the introducer port.

In one embodiment, the ablation probe can comprise a plurality of vapor ports.

In another embodiment, at least part of the introducer probe and at least part of the ablation probe can have complementary shapes preventing rotation of the ablation probe with respect to the introducer.

DETAILED DESCRIPTION OF THE INVENTION

A vapor energy generation system is provided that can be configured for introduction into a patient's urethra or prostate, or can be configured to access prostatic tissue transrectally or endoscopically. The system is configured to deliver a heated condensable vapor, for example water vapor, to tissue as described in the following co-pending U.S. patent applications: U.S. patent application Ser. No. 10/681,625, filed Oct. 7, 2003, titled "Medical Instruments and Techniques for Thermally-Mediated Therapies"; Ser. No. 11/158, 930 filed Jun. 22, 2005, titled "Medical Instruments and Techniques for Treating Pulmonary Disorders"; Ser. No. 11/244, 329, filed Oct. 5, 2005, titled "Medical Instrument and Method of Use"; and Ser. No. 11/329,381, filed Jan. 10, 2006, titled "Medical Instrument and Method of Use".

The generation and delivery of a collapsible, high energy vapor for various therapeutic procedures is further disclosed in systems with 'remote" vapor generation systems or sources in co-pending Provisional Patent Application Nos. 60/929, 632, 61/066,396, 61/068,049, or with vapor generator in a handle or working end, or combination thereof, as described in Provisional Patent Application Nos. 61/068,130, 61/123, 384, 61/123,412, 61/126,651, 61/126,612, 61/126,636, 61/126,620.

Figure 1:
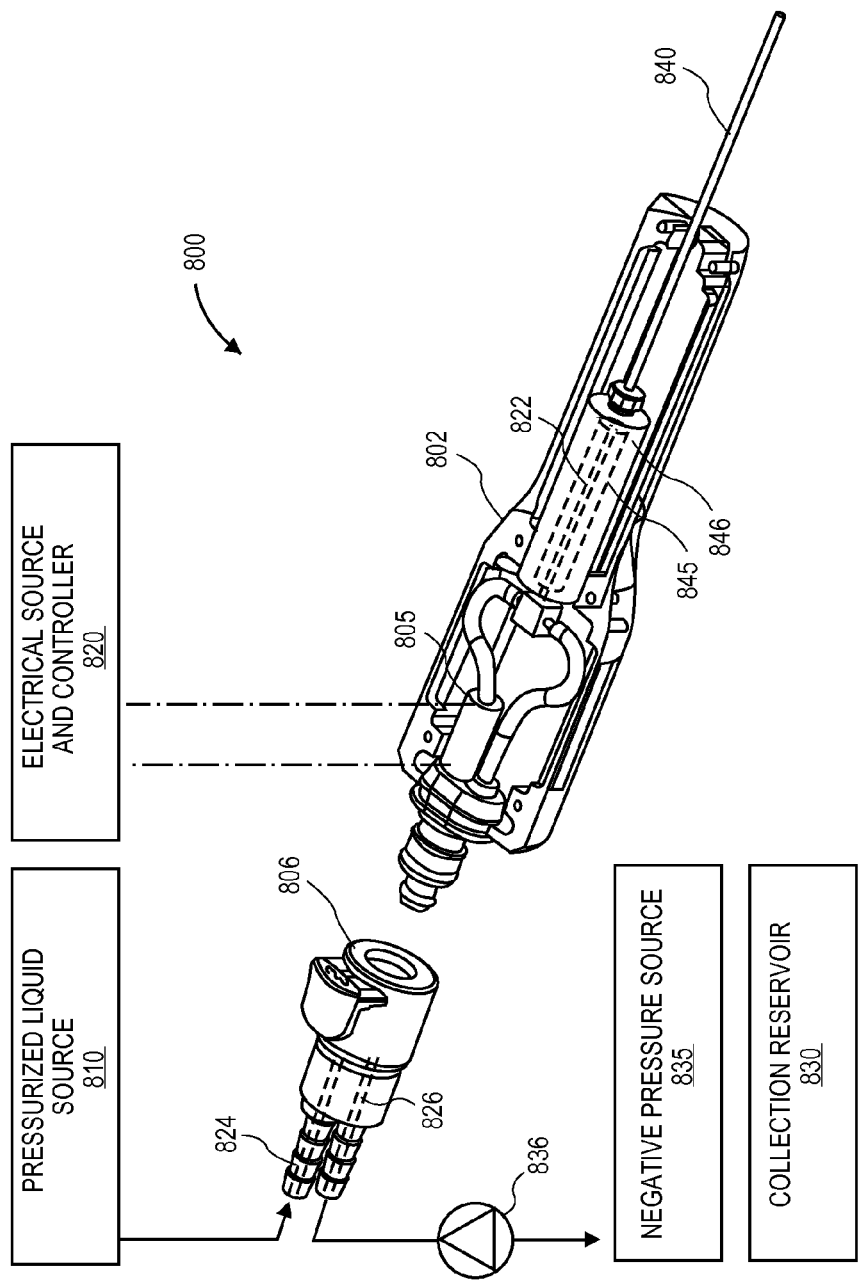
FIG. 1 is a cut-away view of vapor energy delivery system including a handle portion of an instrument with an inductive heating assembly for applying vaporization energy to a fluid flow together with a looped flow system for maintaining a circulating flow of high energy vapor which is releasable on demand to flow through an extension member to interact with tissue.

FIG. 1 illustrates a vapor energy generation system 800 having a handle 802 comprising an inductive heating system similar to that described in applications 61/123,416, 61/123, 417, 61/126,647. In FIG. 1, the handle 802 is coupled by temperature resistant fitting 806 to a fluid source 810 that delivers liquid at a controlled flow rate and pressure. The liquid flow passes through a vapor generating inductive heater 805 coupled to an electrical source and controller 820. The system and handle is configured for a looped liquid/vapor flow to provide vapor to working end or exit channel 822 to deliver the vapor to a tissue site. The system has inflow channel indicated at 824 and outflow channel at 826 that can communicate with a collection reservoir 830 and/or a negative pressure source 835. A valve 836, for example, operated by a footswitch is provided in outflow channel 826 to re-direct vapor into the exit channel 822 and extension member 840.

A vapor energy generation system 800 as shown in FIG. 1 can be used for any surgical/medical application, with the extension member 840 comprising a needle, an elongate ablation probe, a flexible catheter, or other similar elongate delivery devices. This system can be used for a catheter for delivering energy for endovascular applications, for treating respiratory tract disorders, for endometrial ablation treatments or for needle ablation treatments. In the embodiment of FIG. 1, an optional secondary heater 845 is shown with a concentric insulator 846. This secondary heater can add further vaporization energy to vapor that starts to flow through exit channel 822. The secondary heater can be an inductive heater or a resistive heater that uses a microporous material to provide a large surface area to apply energy to the vapor to remove any water droplets. This system can provide a vapor that is at least 90% water vapor. The secondary heater is operatively coupled to the electrical source and controller 820 by electrical leads (not shown).

Figure 2:
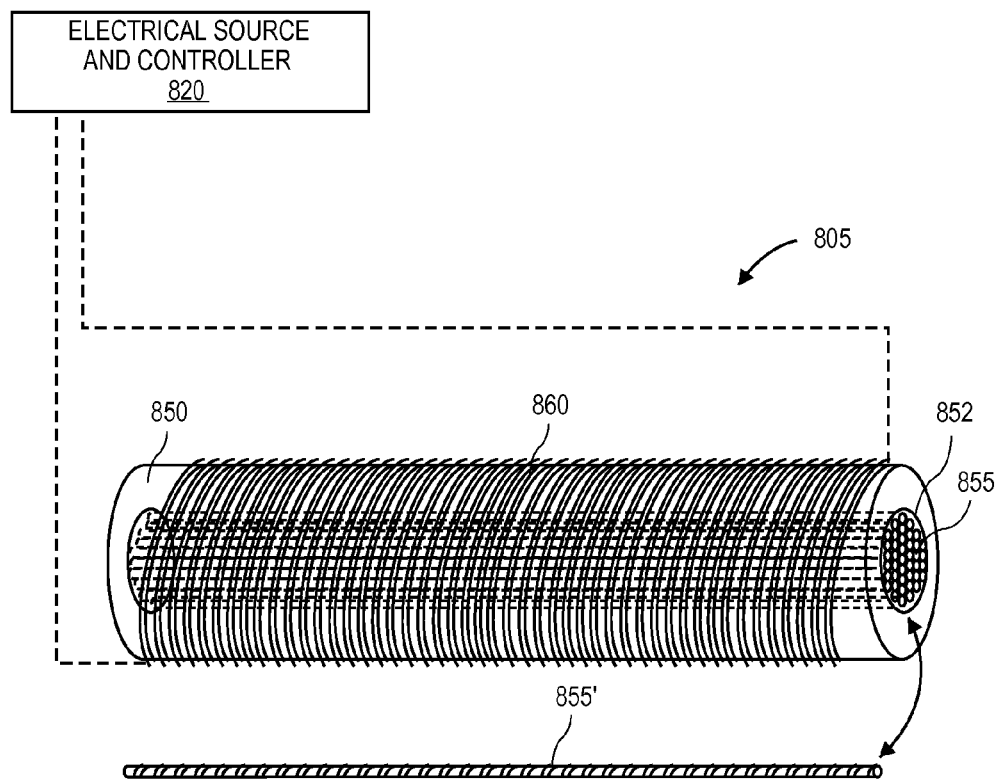
FIG. 2 is a schematic view of the inductive heating assembly of FIG. 1.

FIG. 2 illustrates a vapor generating inductive heater 805 that in on embodiment comprises a ceramic cylinder 850 with a bore 852 therein. The ceramic cylinder 850 can be approximately 1.0" to 1.5" in length and 0.25" in diameter with a 0.10" bore 852, for example. The bore 852 is packed with a plurality of small diameter hypotubes 855 that are magnetic responsive, such as 316 stainless steel, for example. In one embodiment, the hypotubes 855 are 0.016 thin wall tubes. A winding 860 of one to ten layers having and an axial length of about 1.0" is provided about the ceramic cylinder 850 for inductive heating of the hypotubes 855 using very high frequency current from an electrical source. In one embodiment the winding 860 can be 26 Ga. Copper wire with a Teflon coating. It has been found that delivering at least 50 W, 100 W, 200 W, 300 W, or 400 W with suitable flow rates of water can produce very high quality vapor, for example 90% vapor and better.

In FIG. 2, it can be seen that an inductively heated hypotube 855' also can be spiral cut to provide flexibility for such an inductive heater to be positioned in a catheter or probe working end. For example, such flexible heatable elements can be carried in the bore of a flexible high temperature resistant polymeric insulative member such to provide a flexible catheter that is configured for endovascular navigation. An insulation layer about an exterior of the inductive heater is not shown. In general, the vapor generating inductive heater 805 can configured to provide a high quality vapor media with precise parameters in terms of vapor quality, exit vapor pressure from a working end, exit vapor temperature, and maintenance of the parameters within a tight range over a treatment interval. All these parameters can be controlled with a high level of precision to achieve controlled dosimetry, whether the particular treatment calls for very low pressures (e.g., 1-5 psi) or very high pressures (200 psi or greater) over a treatment interval, and whether the treatment interval is in the 1-10 second range or 2 to 5 minute range.

FIGS. 3-7 illustrate a prostate therapy system, including a vapor source 100 operatively connected to an elongated instrument or introducer 102 with imaging system 104. The vapor source 100 can be a condensable vapor source, or other appropriate energy sources. The prostate therapy system can be introduced into a patient urethra 105 within prostate 106 and navigated to a predetermined location. The distal end of the instrument and imaging system 104 can be used to identify anatomical landmarks during insertion. The imaging system can be an endoscope or CCD as known in the art. In one embodiment, the introducer 102 can include an extending member 110 that extends through the urethra, and distal expandable structure such as balloon 112, which can assist in stabilizing the assembly within the prostate and axially register the assembly relative to anatomic landmarks and structures such as the bladder.

Figure 3:
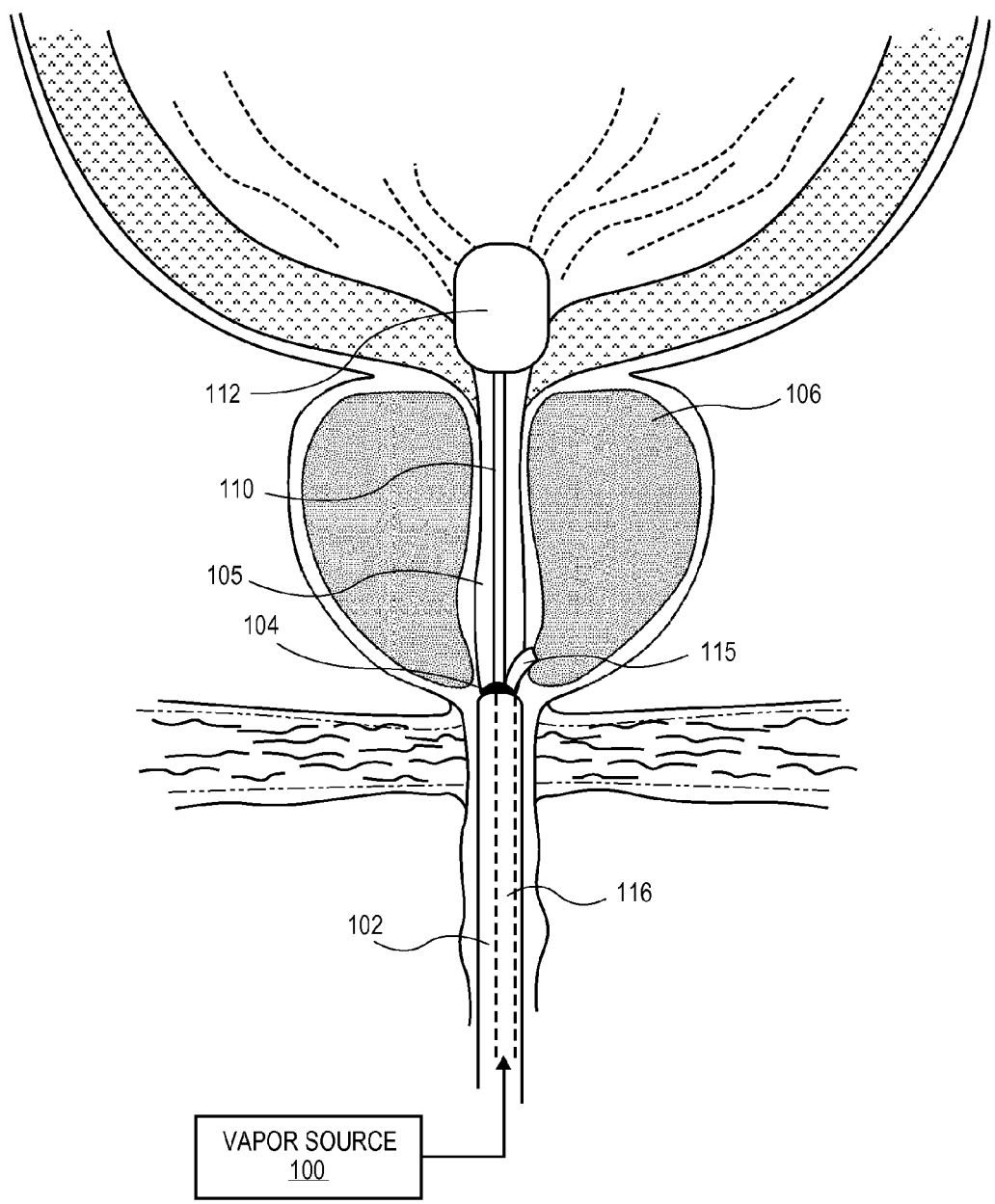
FIG. 3 is a schematic view of a patient prostate and a first step of introducing a vapor delivery tool or needle into a proximal aspect of the prostate, wherein the first step includes advancing a distal port to engage the lumen wall at a selected location.

Referring to FIG. 3, a distal port 115 that can be straight or can have a memory curved configuration is extended from a channel 116 in introducer 102 to engage tissue about the urethra while viewing through the imaging system 104. The prostate therapy system can include irrigation and aspiration means (not shown) to flow a fluid such as sterile water or saline into and through the urethra 105. The distal port is extended when the desired location in the urethra is identified and engaged under slight or moderate pressure of the distal port 115 against the inner wall of the urethra. The distal port may be extended 'slightly' outward of channel 116 or can be extended 5 mm or 10 mm or more from the channel.

Figure 4:
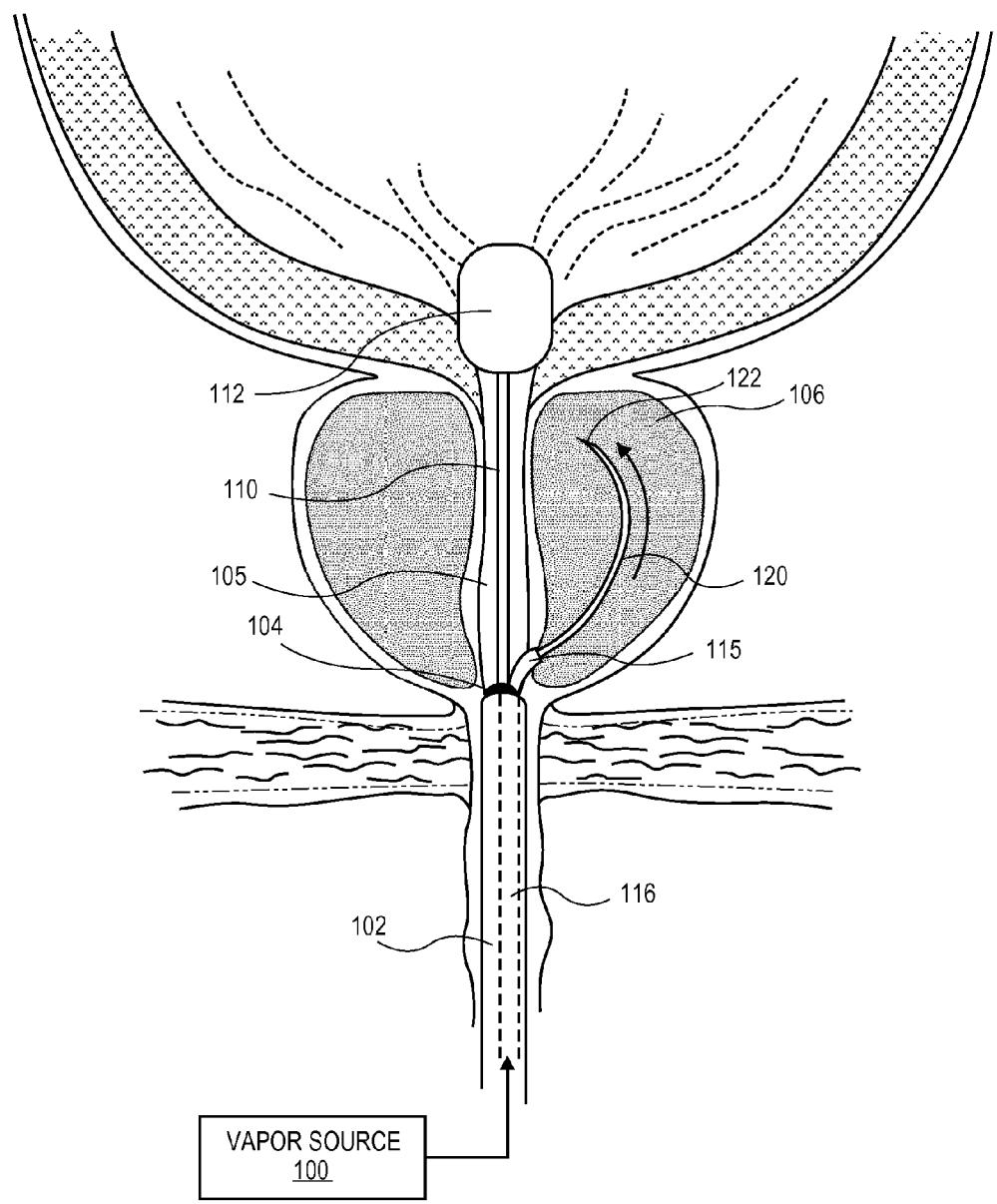
FIG. 4 is a schematic view of the patient prostate of FIG. 3 with a subsequent step of introducing a sharp-tipped needle or ablation probe into the proximal aspect of the prostate through the distal port member.

As can be seen in FIG. 4, a vapor delivery needle or ablation probe 120 is extended through the distal port 115 into the prostate 106. The ablation probe can be operatively connected to the vapor source 100 to deliver energy to ablate prostate tissue. The ablation probe can be adapted to be inserted transurethrally into a prostate lobe of a male subject. In some embodiments, the probe can be adapted to be inserted substantially parallel to the prostatic urethra region of the subject. The probe 120 can have a configuration with at least one curve that allows the working end 122 of the probe 120 having a curved or straight axis to extend substantially parallel to the prostatic urethra 105, rather than more transverse to the axis of the urethra. In some embodiments, the ablation probe is configured to be advanced through the urethral wall into an apex of the prostate lobe.

Figure 5:
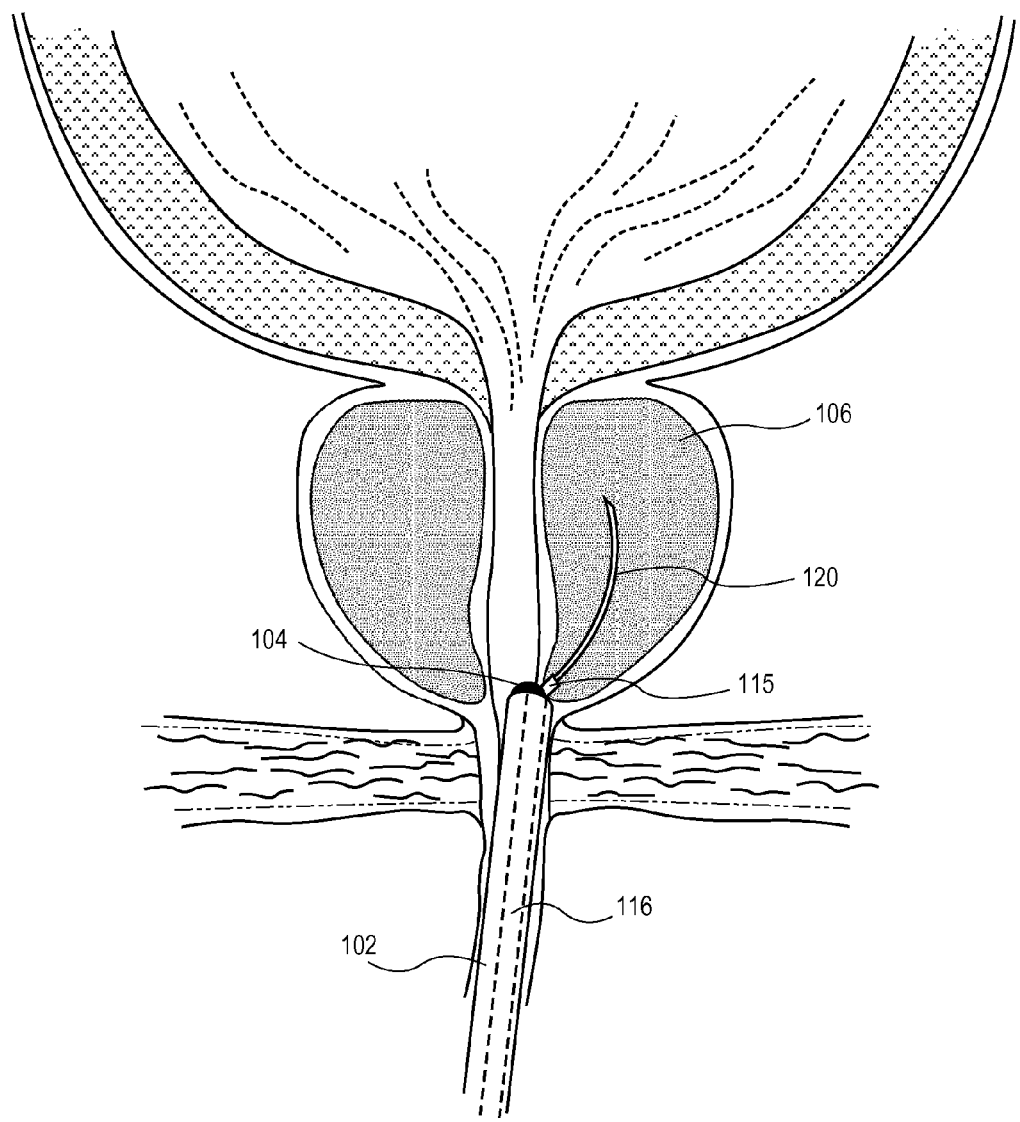
FIG. 5 is a schematic view of a patient prostate and another method of introducing an ablation probe into a proximal aspect of the prostate.

The configuration of the probe working end 122 is adapted for vapor energy delivery and for controlling the geometry of the tissue ablated by the interstitial vapor propagation. In one embodiment, the vapor propagation and region of tissue ablation is elongated and substantially parallel to the urethra. In another embodiment, the vapor propagation and region of tissue ablation extends substantially the length of the urethra through the prostate. In another embodiment, the vapor propagation and region of tissue ablation does not extend to peripheral regions of the prostate capsule except about the urethra. In another embodiment, the vapor propagation and region of tissue ablation does not allow heating of prostate tissue about the prostatic capsule which is adjacent nerves and nerve bundles. The treated tissue geometry is thus optimized for ablation and resorption of prostatic tissue adjacent the urethra without damage to prostate tissue not adjacent the urethra. The procedure described above is repeated to ablate tissue in the opposing prostate lobe. FIG. 5 depicts a method of angling an introducer 102' to better enable advancement of an ablation probe 120 into the prostate.

Figure 6:
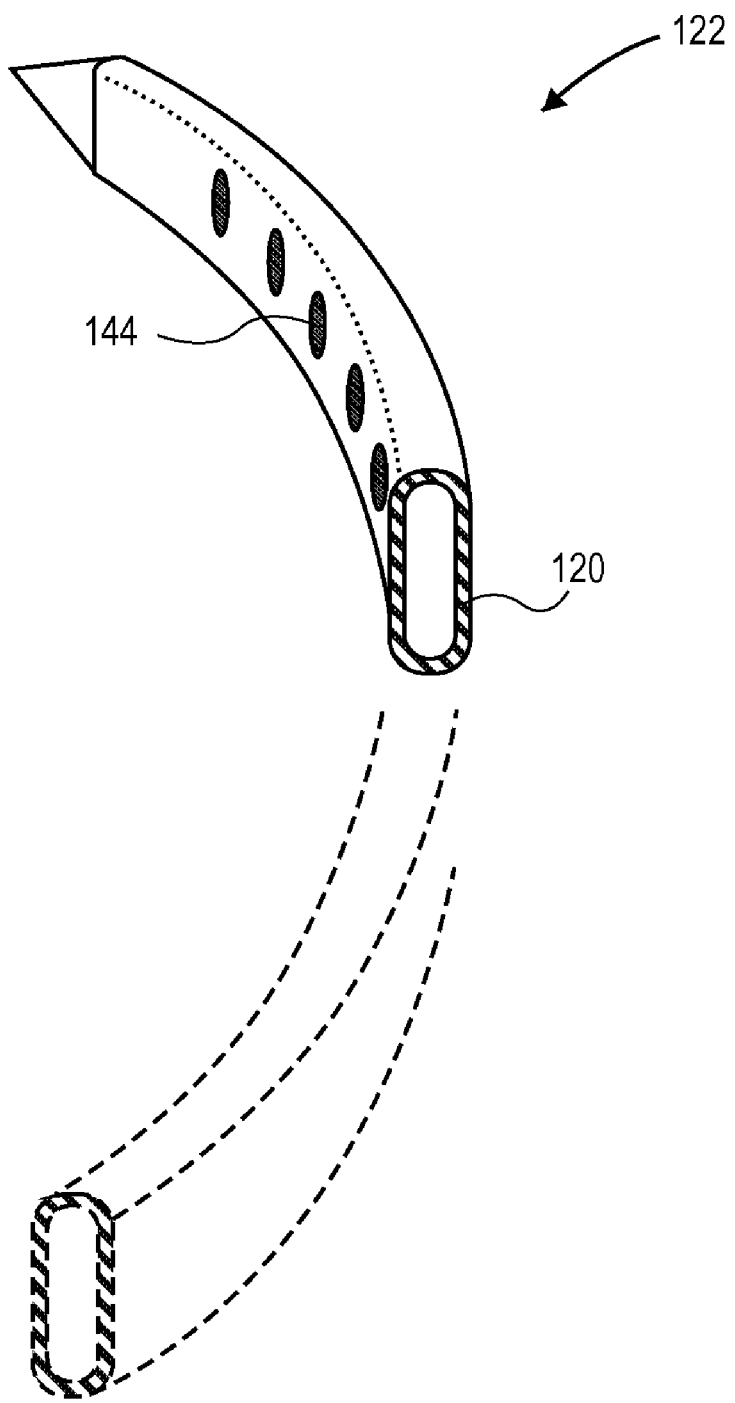
FIG. 6 is a sectional perspective view of the working end of one embodiment of an ablation probe such as the probe depicted in FIGS. 4-5.

FIG. 6 is a sectional perspective view of the working end of one embodiment of a needle or ablation probe 120. In FIG. 6, the probe 120 and working end 122 have a non-round cross section to prevent rotation relative to the introducer (not shown). The probe 120 can be fabricated of a biocompatible stainless steel or NiTi with a predetermined shape to accomplish to objectives described above. In one embodiment, the working end 122 of the probe carries a plurality of vapor outlets or ports 144 asymmetrically relative to the needle axis and more particularly has vapor outlets oriented to direct vapor flow inwardly toward the urethra. The vapor ports 144 can number from about 2 to 50 and can have mean diameters ranging from about 0.001" to 0.05". In a round probe 120 with a keyed shaft, the hollow needle diameter can range from about 40 ga. to 11 ga., with a similar flow cross section in non-round needles as in FIG. 6. As can be seen in FIG. 6, the probe can be rectangular in section with rounded corners, or alternatively can be oval or round in shape. In a non-round probe, the major axis of the cross-section can be greater that about 1.5× the minor axis of the cross section.

Figure 7:
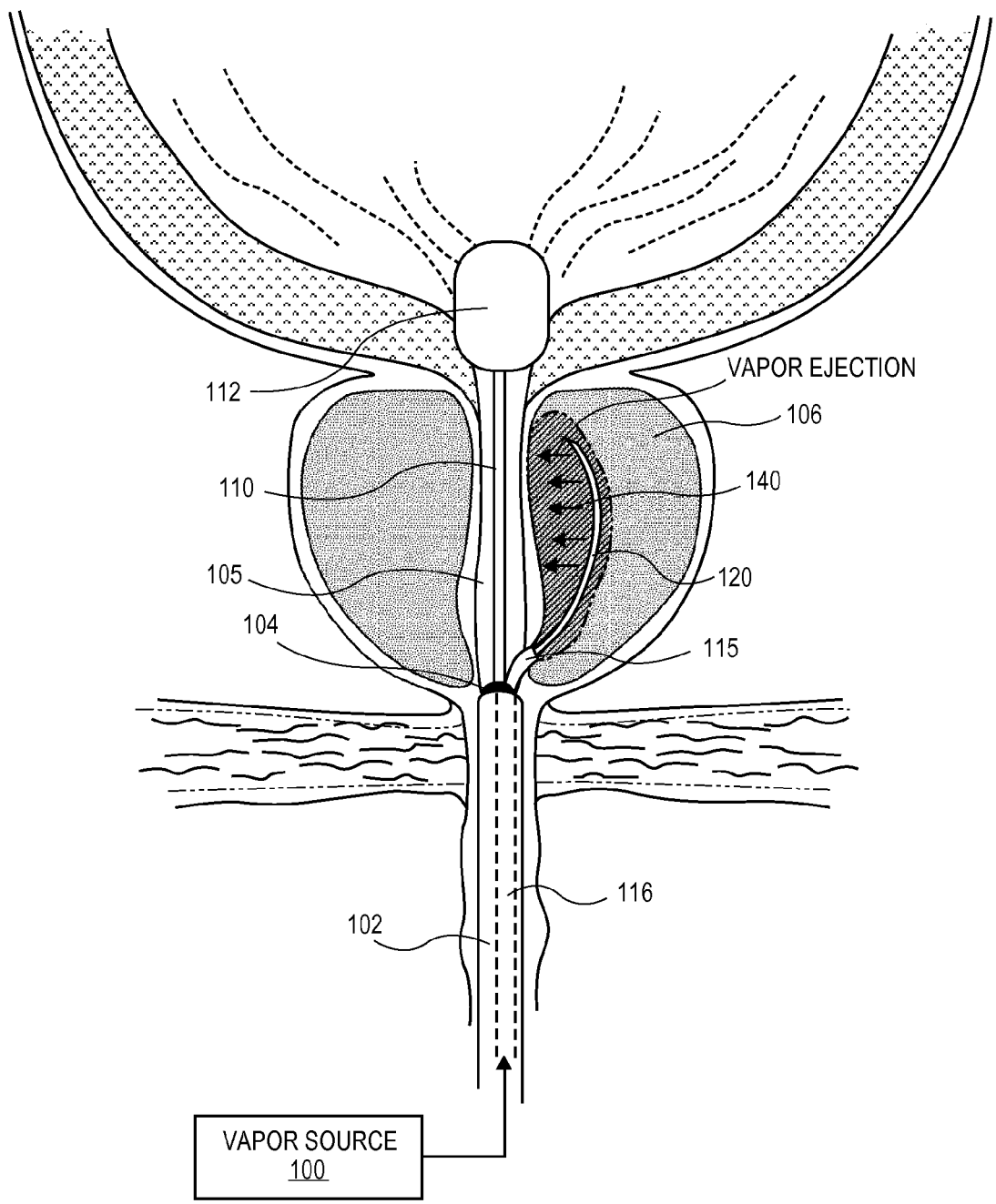
FIG. 7 is a schematic view of the patient prostate as in FIG. 4 with the delivery of vapor energy to create an ablation region proximate the urethra.

In FIG. 7, the vapor propagation is depicted with an ablated tissue volume about the urethra indicated at 140. For example, a needle or ablation probe 120 having vapor ports 144 as illustrated in FIG. 6 can allow vapor flowing through the probe to be directed towards the urethra from within the prostatic tissue of a prostatic lobe. In order to achieve the directional propagation of vapor media as in FIG. 7, the probe 120 and its working end are further configured for rotational or angular registration with the distal port 115 and introducer 102 as described above. This aspect can be accomplished by at least a portion of the shaft of probe 120 within the introducer 102 having a 'key' that is slidable within channel 116 to prevent relative rotation between the probe shaft and the introducer. Thus, at least part of the introducer and at least of the ablation probe can have complementary shapes to prevent rotation of the ablation probe with respect to the introducer.

In general, a method for vapor delivery to ablate prostate tissue introducing a vapor delivery tool or needle into prostate tissue, and applying at least 20 W, 50 W, 100 W, 200 W, 400 W, or 600 W from the tool by means vapor energy release to ablate tissue. In one embodiment, the method applies energy that is provided by a condensable vapor that undergoes a phase change to provide applied energy of at least 100 cal/gm, 250 cal/gm, 300 cal/gm, 350 cal/gm, 400 cal/gm and 450 cal/gm of the vapor.

Figures 8A, 8B:
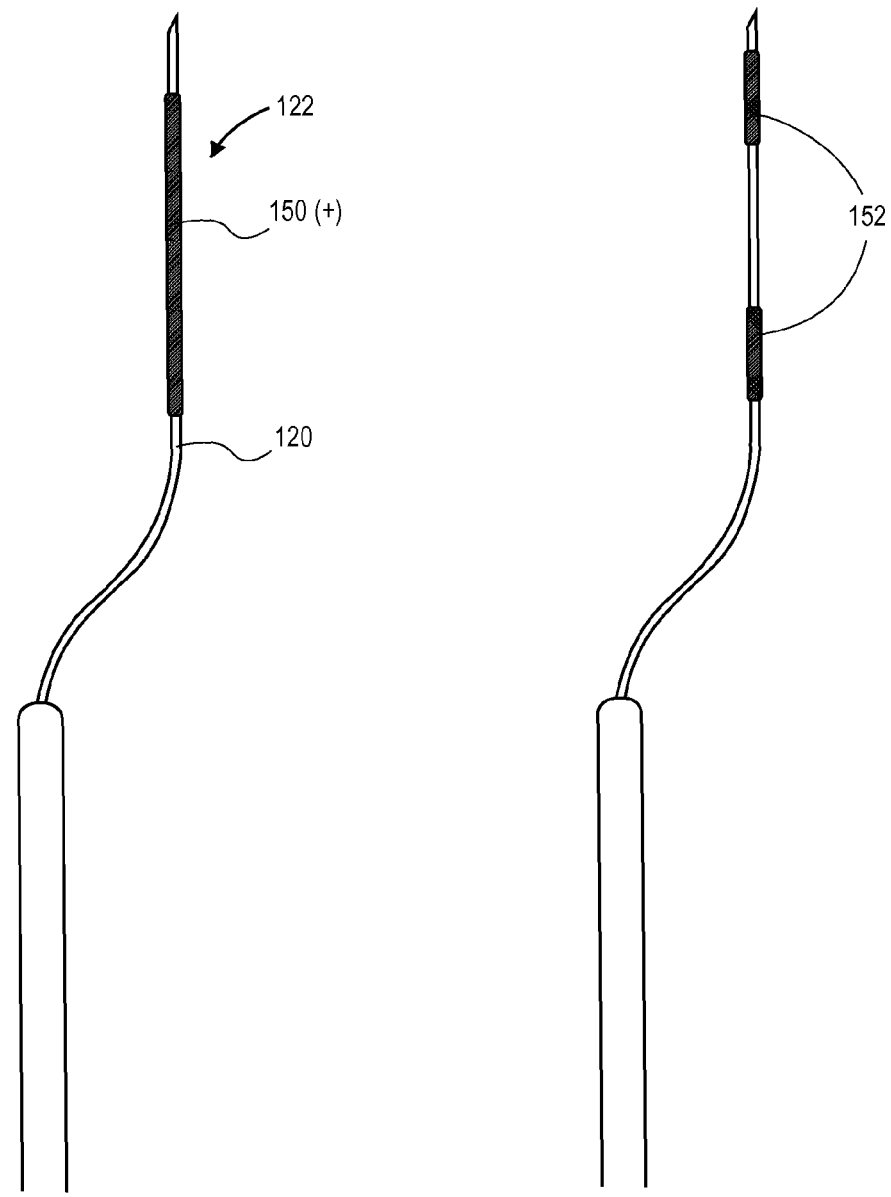
FIG. 8A is an ablation probe with an electrode for applying additional energy to tissue.
FIG. 8B is an ablation probe with a bi-polar electrode arrangement.
Figure 8C:
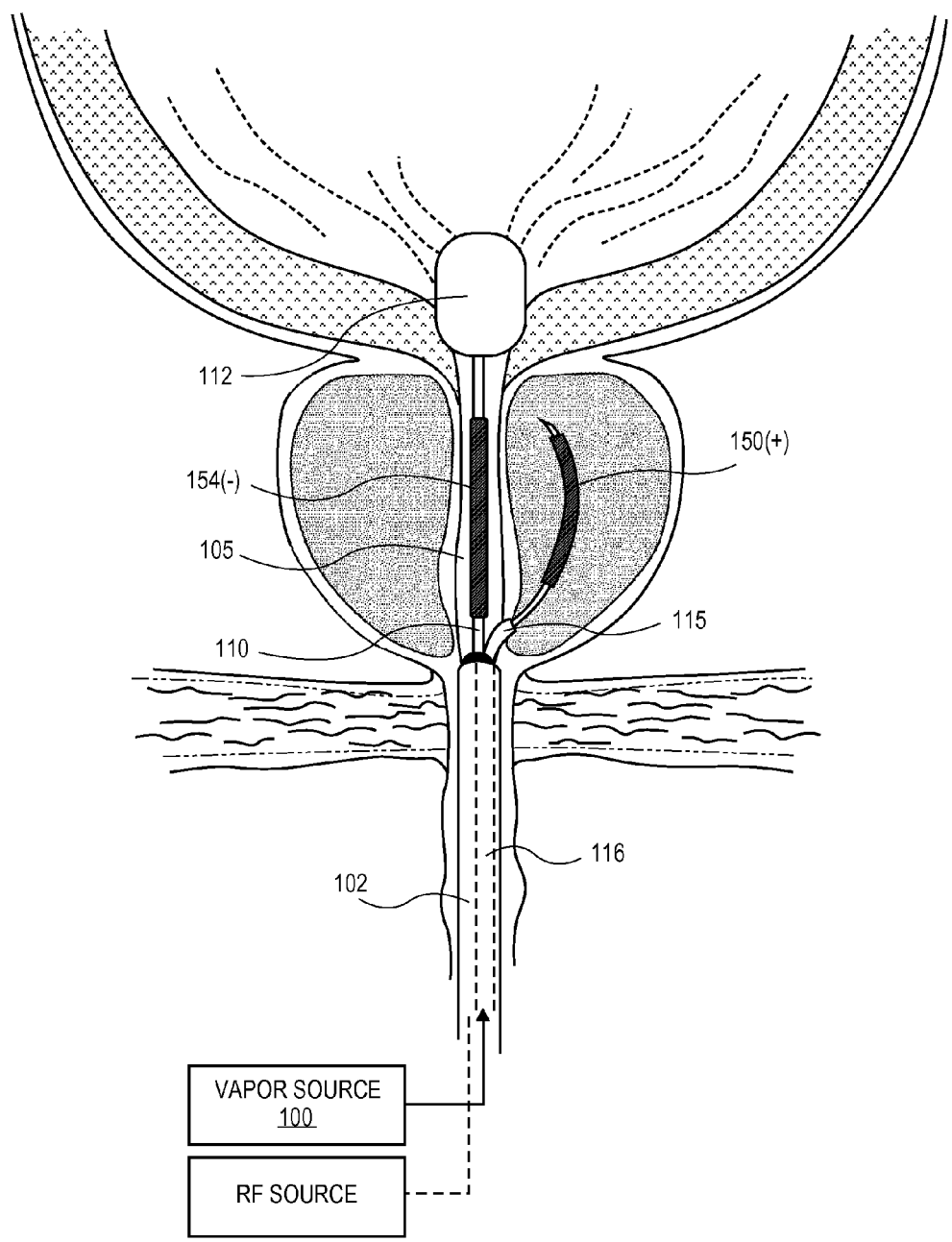
FIG. 8C is an ablation probe with an electrode that cooperates with an electrode within the urethra.

In another embodiment shown in FIGS. 8A-8B, the working end 122 of needle or ablation probe 120 can carry a mono-polar electrode 150 or a bi-polar electrode arrangement 152 to further apply energy to tissue. Alternatively, as shown in FIG. 8C, an electrode 154 can be carried the elongate extending member 110 or a hypertonic saline electrode in the urethra can comprise a return electrode to cooperate with an electrode 150.

In general, a method for treating a disorder of the prostate comprises introducing an ablation probe into a lobe of the prostate, and ablating prostatic tissue within the lobe. The ablation probe can ablate the prostatic tissue by delivering condensable vapor through the probe into the prostate lobe. The ablation probe can ablate prostate tissue within the lobe without ablating tissue of the prostatic urethra.

To gain access to the prostate, an introducer can be advanced transurethrally into the urethra, and the ablation probe can be advanced through the introducer. In one embodiment, a port of the introducer can be placed against the urethral wall prior to advancing the ablation probe through the introducer. In one embodiment, at least part of the introducer and at least part of the ablation probe can have complementary shapes preventing rotation of the ablation probe with respect to the introducer. In some embodiments, the ablation probe can be introduced into a lobe of the prostate substantially parallel to a prostatic urethra. In some embodiments, the ablation probe can be advanced through a urethral wall into an apex of the prostate lobe. The ablation probe can be advanced at least 15 mm into the prostate lobe, for example. In some embodiments, the condensable vapor can be delivered into the prostate lobe through a plurality of vapor ports in the ablation probe. The vapor ports can be oriented towards the urethra, for example.

These methods can utilize condensable vapor to deliver between 100 and 10,000 Joules to the prostate lobe. In other embodiments, the condensable vapor can deliver between 100 W and 400 W to the prostate lobe, or alternatively, between 20 W and 1000 W to the prostate lobe. In some embodiments, the condensable vapor can deliver between 250 cal/gm and 450 cal/gm to the prostate lobe, or alternatively, between 100 cal/gm and 600 cal/gm to the prostate lobe. The methods can cause localized ablation of prostate tissue, and more particularly the applied energy from vapor can be localized to ablate prostate tissue adjacent the urethra without damaging prostate tissue that is not adjacent the urethra.

The handle of an integrated system for prostate treatment with vapor delivery (not shown) can be configured with sliders, levers, grips etc for actuating the (i) extension of a distal port, (ii) the advancement of an ablation probe from the distal port, and (iii) the delivery of vapor for a selected treatment interval. All these systems can be manually actuated, robotic or computer controlled.

In another embodiment, a method for treating a prostate disorder comprises introducing a thermal energy delivery member into prostate tissue proximate an anterior aspect of the urethra within the prostate and advancing the member distal end to a location proximate a posterior aspect of the urethra within the prostate, and applying energy from the needle to ablate prostate tissue adjacent the urethra. Again, the energy delivery member can include means to deliver a heated vapor.

In another embodiment, a method for treating a prostate disorder comprises introducing a vapor delivery tool into prostate tissue proximate an anterior aspect of the urethra within the prostate and advancing the tool distal end at substantially parallel to the urethra within the prostate, and introducing vapor from the tool to ablate prostate tissue adjacent the urethra.

In another embodiment, a method for treating a prostate disorder comprises introducing a vapor delivery needle into prostate tissue proximate an anterior aspect of the urethra within the prostate and advancing the needle substantially non-transverse relative to an axis of the urethra.

In another embodiment, a method for treating a prostate disorder comprises introducing a vapor delivery needle into prostate tissue proximate an anterior aspect of the urethra within the prostate and advancing the needle at least 15 mm or at least 20 mm within prostate tissue.

In another embodiment, a method for treating a prostate disorder comprises introducing a vapor delivery needle into prostate tissue proximate an anterior aspect of the urethra within the prostate and advancing a non-linear shaped needle in a controlled path in the tissue, wherein the needle is keyed relative to an introducer to prevent rotation of the needle.

In another embodiment, a method for treating a prostate disorder comprises introducing a dull-tipped distal port into a patient urethra, pressing the distal port tip into a targeted location in the wall of the urethra, and advancing a sharp-tipped needle from the distal port and through the wall or the urethra, and delivering energy from the needle to ablate prostate tissue. The needle can be advanced from the distal port by means of a manual actuation or preferably can have a spring-loaded or other robotic actuation of the needle. In one embodiment, a spring-actuated movement of the needle tip is provided to advance the needle tip through the urethra in a first extension distance, and a second extension distance is accomplished by means of manual actuation.

In another embodiment, the introduction of the needle and the delivery of vapor can be accomplished under any suitable type of imaging. In one method, the steps can be viewed by means of ultrasound or x-ray imaging. In one method, the needle introduction and energy delivery methods can be imaged by ultrasound utilizing a trans-rectal ultrasound system.

In another embodiment, the system may be used to delivery of fluids for to specific locations in the prostate for medical purposes, such as for general or localized drug delivery, chemotherapy, or injections of other agents that may be activated by vapor or heat.

As for additional details pertinent to the present invention, materials and manufacturing techniques may be employed as within the level of those with skill in the relevant art. The same may hold true with respect to method-based embodiments in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of treating a disorder of a prostate adjacent a prostatic urethra, the method comprising:
   advancing a vapor ablation probe transurethrally into the prostate;
   delivering condensable vapor into the prostate, the condensable vapor undergoing a phase change to deliver between 100 and 10,000 Joules to the prostate; and
   ablating prostate tissue without ablating the prostatic urethra.

2. The method of claim 1 wherein the advancing step comprises advancing the vapor ablation probe into an apex of a lobe of the prostate.

3. The method of claim 1 wherein the condensable vapor delivers between 100 W and 400 W to the prostate.

4. The method of claim 1 wherein the condensable vapor delivers between 250 cal/gm and 450 cal/gm to the prostate.

5. The method of claim 1 wherein the condensable vapor delivers between 20 W and 100 W to the prostate.

6. The method of claim 1 wherein the condensable vapor delivers between 100 cal/gm and 600 cal/gm to the prostate.

7. The method of claim 1 wherein the introducing step comprises advancing the ablation probe at least 15 mm into the prostate.

8. The method of claim 1 wherein the introducing step comprises introducing condensable vapor into the prostate through a plurality of vapor ports in the ablation probe.

9. The method of claim 8 wherein the introducing step comprises orienting the vapor ports toward the urethra.

10. The method of claim 1 wherein the introducing step comprises advancing an introducer into a urethra and advancing the ablation probe through the introducer.

11. The method of claim 10 further comprising placing a port of the introducer against a urethral wall prior to advancing the ablation probe through the introducer.

12. The method of claim 10 wherein at least part of the introducer probe and at least part of the ablation probe have complementary shapes preventing rotation of the ablation probe within the introducer.

* * * * *

UNITED STATES PATENT AND TRADEMARK OFFICE
CERTIFICATE OF CORRECTION

| | | |
|---|---|---|
| PATENT NO. | : 8,251,985 B2 | Page 1 of 1 |
| APPLICATION NO. | : 12/614218 | |
| DATED | : August 28, 2012 | |
| INVENTOR(S) | : Hoey et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 287 days.

Signed and Sealed this
Twenty-ninth Day of January, 2013

David J. Kappos
*Director of the United States Patent and Trademark Office*